US 7,588,941 B2
Sep. 15, 2009

(12) United States Patent
Zheng et al.

(54) DISPERSION OF CARBON NANOTUBES BY NUCLEIC ACIDS

(75) Inventors: Ming Zheng, Wilmington, DE (US); Bruce A. Diner, Chadds Ford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 295 days.

This patent is subject to a terminal disclaimer.

(21) Appl. No.: 11/590,564

(22) Filed: Oct. 31, 2006

(65) Prior Publication Data

US 2007/0134696 A1 Jun. 14, 2007

Related U.S. Application Data

(62) Division of application No. 10/716,346, filed on Nov. 18, 2003, now Pat. No. 7,498,423.

(60) Provisional application No. 60/428,087, filed on Nov. 21, 2002, provisional application No. 60/432,804, filed on Dec. 12, 2002.

(51) Int. Cl.
*C12Q 1/68* (2006.01)
*C12M 1/00* (2006.01)
*C07H 21/04* (2006.01)

(52) U.S. Cl. .................. 436/6; 435/283.1; 435/287.2; 536/23.1; 536/24.1; 536/24.3

(58) Field of Classification Search .................. None
See application file for complete search history.

(56) References Cited

U.S. PATENT DOCUMENTS

| 5,650,277 | A | 7/1997 | Navot et al. |
| 5,866,434 | A | 2/1999 | Massey et al. |
| 6,159,742 | A | 12/2000 | Lieber et al. |
| 6,821,730 | B2 | 11/2004 | Hannah |
| 7,374,649 | B2 * | 5/2008 | Jagota et al. ............... 204/456 |
| 2005/0019791 | A1 | 1/2005 | Jung et al. |
| 2005/0053966 | A1 | 3/2005 | Poponin |
| 2005/0164211 | A1 | 7/2005 | Hannah |
| 2005/0181409 | A1 | 8/2005 | Park et al. |

FOREIGN PATENT DOCUMENTS

WO    WO 02/076888 A1    10/2002

OTHER PUBLICATIONS

Fukushima, Takanori et al., Molecular Ordering of Organic Molten Salts Triggered by Single-Walled Carbon Nanotubes, Science, Jun. 27, 2003, p. 2072-2074, vol. 300.
Lui et al., Fullerene Pipes, Science 280, 1253, 1998.
O'Connell et al., Reversible water-solubilization of single-walled carbon nanoChem. Phys. Lett., 342, 265, 2001.
Bandow et al., Purification of Single-Wall Cabon Nanotubes by Microfiltration, J. Phys. Chem. B 101, 8839, 1997.
Chen et al., Solution Properties of Single-Walled Carbon Nanotubes, Science 282, 95, 1998.
Duesberg et al., Chromatographic size separation of single-wall carbon nanotubes Appl. Phys. A 67, 117, 1998.
Dalton et al., Selective Interaction of a Semiconjugated Organic Polymer with Single-Wall Nanotubes, J. Phys Chem. B104 10012, 2000.
Dalton et al., A functional conjugated polymer to process, purify and selectively interact with single wall carbon nanotubes, Synth. Metals 121, 1217, 2001.
Bandyopadhyaya et al., Stabilization of Individual Carbon Nanotubes in Aqueous Solutions, Nano Lett. 2, 25, 2002.
O'Connell et al., Band Gap Fluorescence from Individual Single-Walled Carbon Nanotubes, Science 297, 593, 2002.
Williams et al., Towards DNA-Mediated Self Assembly of Carbon Nanotube Molecular Devices, AIP Conf. Proc. 663, 444, 2002.
Jiang et al., Production of aqueous colloidal dispersions of carbon nanotubes, Journal of Colloid and Interface Science, 2003, 260(1), 89-94.
Wang et al., A treatment method to give separated multi-walled carbon nanotubes with high purity, high crystallization and a large aspect ratio, Carbon, 2003, 41(15), 2939-2948.
Guo et al, Immobilization and Visualization of DNA and Proteins on Carbon Nanotubes, Advanced Materials, 1998 10(9), 701-703.
Tsang et al., Immobilization of Platinated and Iodinated Oligonucleotides on Carbon Nanotubes, Angew, Chem Int., 1997, 36(20), 2198-2200.

* cited by examiner

*Primary Examiner*—B J Forman

(57) ABSTRACT

Nucleic acid molecules in a stabilized solution such as single stranded DNA and RNA were able to disperse high concentration of bundled carbon nanotubes into aqueous solution.

10 Claims, 7 Drawing Sheets

Dispersion of Carbon Nanotubes by Single-stranded DNA

Sonication time and addition of denaturants on dispersion of carbon nanotubes

Dispersion of carbon nanotubes by ssDNA versus surfactant

5A. Biotin-N90

5B. N90

Immobilization of DNA Dispersed Carbon Nanotubes through Biotin-Streptavidin Interaction Micrograph of Wrapped Nanotube Micrograph of Different Modes of DNA Wrapping on Nanotubes

DISPERSION OF CARBON NANOTUBES BY NUCLEIC ACIDS

This application claims the benefit of U.S. provisional application 60/428,087, filed Nov. 21, 2002 and U.S. provisional application 60/432804, filed Dec. 12, 2002.

FIELD OF INVENTION

The invention relates the use of biopolymers to disperse carbon nanotubes for use in nanodevices. More specifically nucleic acid molecules have been found to disperse bundled carbon nanotubes.

BACKGROUND

Carbon nanotubes (CNT) have been the subject of intense research since their discovery in 1991. CNT's possess unique properties such as small size and electrical conductivity, which makes them suitable in a wide range of applications, including use as structural materials in molecular electronics, nanoelectronic components, and field emission displays. Carbon nanotubes may be either multi-walled (MWNTs) or single-walled (SWNTs), and have diameters in the nanometer range.

Depending on their atomic structure CNT's may have either metallic or semiconductor properties, and these properties, in combination with their small dimensions makes them particularly attractive for use in fabrication of nanodevices. A major obstacle to such efforts has been the diversity of tube diameters, chiral angles, and aggregation states in nanotube samples obtained from the various preparation methods. Aggregation is particularly problematic because the highly polarizable, smooth-sided fullerene tubes readily form parallel bundles or ropes with a large van der Waals binding energy. This bundling perturbs the electronic structure of the tubes, and it confounds all attempts to separate the tubes by size or type or to use them as individual macromolecular species.

There have been many reports on producing suspensions enriched in individual fullerene tubes (J. Liu et al., *Science* 280, 1253 (1998); M. J. O'Connell et al., *Chem. Phys. Lett.* 342, 265 (2001); S. Bandow et al., *J. Phys. Chem.* B 101, 8839 (1997); J. Chen et al., *Science* 282, 95 (1998); G. S. Duesberg, J. Muster, V. Krstic, M. Burghard, S. Roth, *Appl. Phys.* A 67, 117 (1998); A. B. Dalton et al., *J. Phys. Chem.* B 104, 10012 (2000); A. B. Dalton et al., *Synth. Metals* 121, 1217 (2001); R. Bandyopadhyaya, E. Nativ-Roth, O. Regev, R. Yerushalmi-Rozen, *Nano Lett.* 2, 25 (2002)), available samples have still been dominated by small nanotube bundles. M. O'Connell et al (*Science* 297, 593 (2002)) has described a method based on vigorous treatment with a sonicator followed by centrifugation, primarily yielding individual fullerene nanotubes in aqueous micellar suspensions. Also described are processes (M. O'Connell et al., *Chem. Phys. Lett.*, 342, 265, 2001; WO 02/076888) for the solubilization of carbon nanotubes in water by association with selected polymers, although not all polymers tried were successful.

Once the nanotubes are in a dispersed form suitable for further manipulation, a desirable next step is self-assembly of the nanotubes on a solid substrate. Associating oligonucleotides to carbon nanotubes would allow one to use bimolecular techniques for the positioning of the nanotubes on a substrate. K. A. Williams et al (*AIP Conf. Proc.* 663, 444, 2002) has covalently coupled peptide nucleic acid oligomers to carbon nanotubes and then hybridized this construct to DNA. However, DNA was not directly attached to the nanotubes, nor was dispersion of nanotube bundles observed.

The problem to be solved, therefore, is to provide a method for the facile and inexpensive solubilization and dispersion of bundled carbon nanotubes for use in the fabrication of nanodevices. Applicants have solved the stated problem through the discovery that stabilized solutions of nucleic acid molecules have the ability to disperse and solubilize carbon nanotubes, resulting in the formation of nanotube-nucleic acid complexes. Although complexes of nucleic acids and carbon nanotubes are known, the present complexes are new, in that the association between the nanotube and nucleic acid is non-covalent and not through the interaction of specific functionalized groups.

SUMMARY OF THE INVENTION

The invention provides a method for dispersing a population of carbon nanotubes comprising:
 a) providing a stabilized solution of nucleic acid molecules;
 b) contacting a population of carbon nanotubes with an effective amount of the stabilized nucleic acid solution of step (a) for a time sufficient to disperse the carbon nanotubes; and
 c) optionally recovering the dispersed carbon nanotubes.

In an alternate embodiment the invention provides a method of immobilizing a carbon nanotube comprising:
 a) providing a stabilized solution of nucleic acid molecules, said nucleic acid molecules functionalized with at least one first member of a binding pair;
 b) providing a solid substrate having at least one second member of a binding pair immobilized thereon;
 c) contacting a population of carbon nanotubes with an effective amount of the stabilized nucleic acid solution of step (a) whereby the population of carbon nanotubes is dispersed and whereby each carbon nanotube of the population becomes associated with at least one functionalized nucleic acid molecule of step (a); and
 d) contacting the dispersed, nucleic acid associated carbon nanotubes of step (c) with the solid substrate of step (b) whereby the nucleic acid associated carbon nanotubes are immobilized through the interaction of the first and second binding pairs.

Also provided by the invention is a carbon nanotube—nucleic acid complex comprising an unfunctionalized carbon nanotube bound to a nucleic acid molecule.

BRIEF DESCRIPTION OF THE FIGURES

In FIG. 5A, the ssDNA used for carbon nanotube dispersion is biotinylated N90; where as in FIG. 5B, ssDNA used for carbon nanotube dispersion is unmodified N90.

DETAILED DESCRIPTION OF THE INVENTION

Figure 1:
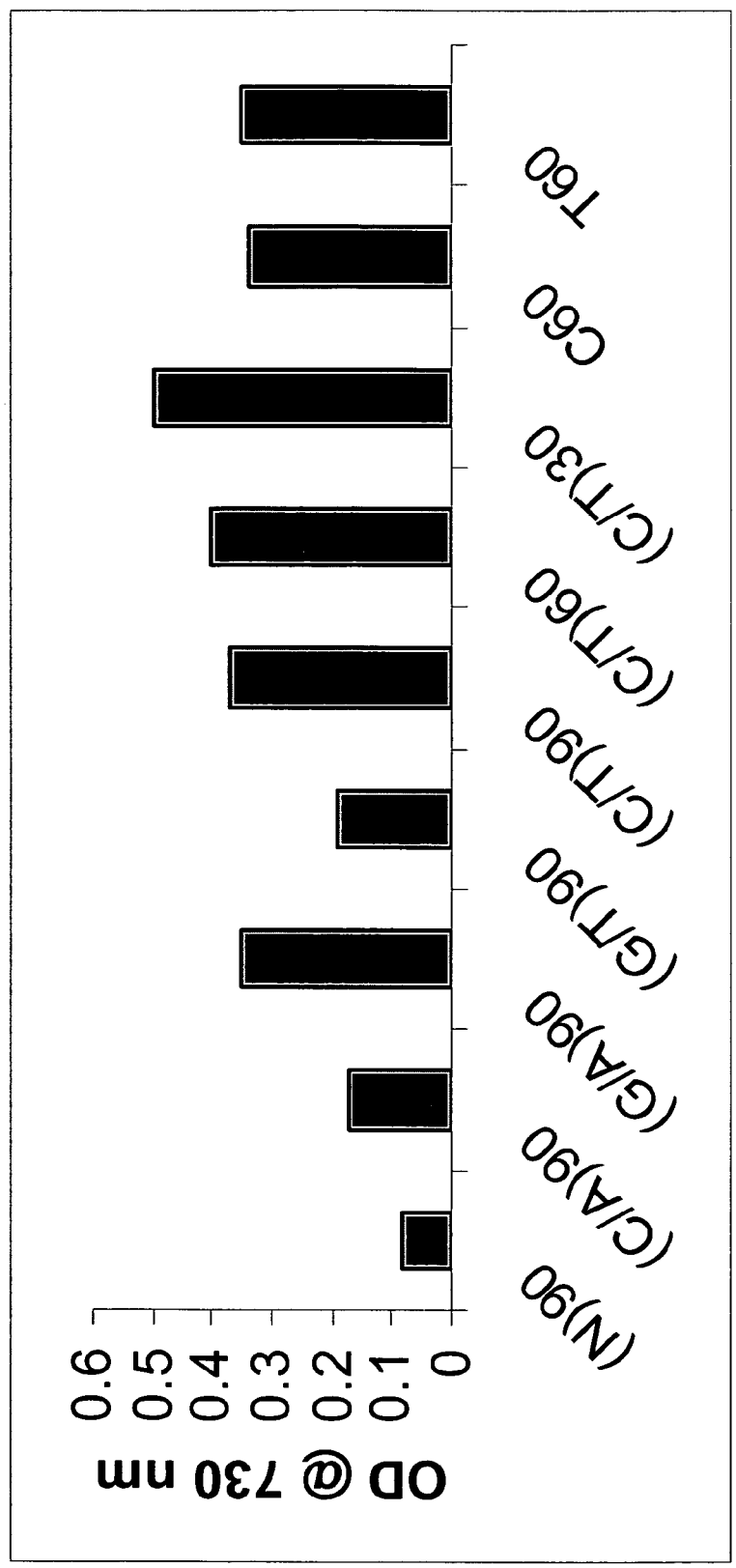
FIG. 1 is a graph of optical density measurements to illustrate the carbon nanotube dispersion efficiency by a variety of sequences.

The invention relates to a method for dispersing a population of bundled carbon nanotubes by contacting the bundled nanotubes with a stabilized solution of nucleic acid molecules. It has been found that nucleic acids are very effective in dispersing the nanotubes, forming nanotube-nucleic acid complexes based on non-covalent interactions between the nanotube and the nucleic acid molecule.

The method is particularly useful since a major obstacle to the manipulation and use of carbon nanotubes (CNT's) as structural materials has been their poor solubility and their tendency to aggregate in bundles or clusters.

In this disclosure the following terms and abbreviations may be used for the interpretation of the claims and specification.

"cDNA" means complementary DNA
"PNA" means peptide nucleic acid
"SEM" means scanning electron microscopy
"ssDNA" means single stranded DNA
"tRNA" means transfer RNA
"CNT" means carbon nanotube
"MWNT" means multi-walled nanotube
"SWNT" means single walled nanotube
"TEM" means transmission electron microscopy The term "carbon nanotube" refers to a hollow article composed primarily of carbon atoms. The carbon nanotube can be doped with other elements, e.g., metals. The nanotubes typically have a narrow dimension (diameter) of about 1-200 nm and a long dimension (length), where the ratio of the long dimension to the narrow dimension, i.e., the aspect ratio, is at least 5. In general, the aspect ratio is between 10 and 2000.

As used herein a "nucleic acid molecule" is defined as a polymer of RNA, DNA, or peptide nucleic acid (PNA) that is single-or double-stranded, optionally containing synthetic, non-natural or altered nucleotide bases. A nucleic acid molecule in the form of a polymer of DNA may be comprised of one or more segments of cDNA, genomic DNA or synthetic DNA.

The letters "A", "G", "T", "C" when referred to in the context of nucleic acids will mean the purine bases adenine ($C_5H_5N_5$) and guanine ($C_5H_5N_5O$) and the pyrimidine bases thymine ($C_5H_6N_2O_2$) and cytosine ($C_4H_5N_3O$), respectively.

The term "peptide nucleic acids" refers to a material having stretches of nucleic acid polymers linked together by peptide linkers.

As used herein the term "stabilized solution of nucleic acid molecules" refers to a solution of nucleic acid molecules that are solubilized and in a relaxed secondary conformation.

The term "nanotube-nucleic acid complex" means a composition comprising a carbon nanotube loosely associated with at least one nucleic acid molecule. Typically the association between the nucleic acid and the nanotube is by van der Waals bonds or some other non-covalent means.

The term "binding pair" refers to chemical or biopolymer based couples that bind specifically to each other. Common examples of binding pairs are immune-type binding pairs, such as antigen/antibody or hapten/anti-hapten systems. Suitable binding pairs glutathione-S-transferase/glutathione, 6×histidine Tag/Ni-NTA, streptavidin/biotin, S-protein/S-peptide, cutinase/phosphonate inhibitor, antigen/antibody, hapten/anti-hapten, folic acid/folate binding protein, and protein A or G/immunoglobulins. Another example of a binding pair is a negatively charged phosphate backbone of a nucleic acid molecule, with the second member being a positively charged surface.

The term "ligand" or "reactive ligand" will refer to one member of a binding pair which has been incorporated into the nucleic acid analyte and may include but is not limited to antibodies, lectins, receptors, binding proteins or chemical agents.

The term "agitation means" refers to a devices that facilitate the dispersion of nanotubes and nucleic acids. A typical agitation means is sonication.

The term "denaturant" as used herein refers to substances effective in the denaturation of DNA and other nucleic acid molecules.

The term "solid support" means a material suitable for the immobilization of a nanotube-nucleic acid complex. Typically the solid support provides an attachment of a member of a binding pair through which the complex is capture and immobilized.

The term "hybridization domain" refers to a specific portion of a nucleic acid molecule that is designed to hybridize to a complementary strand of another nucleic acid molecule. "Hybridizable" nucleic acids may be used to immobilize or direct placement of nanotube-nucleic acid complexes in the fabrication of nano-devices.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1°SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

Standard recombinant DNA and molecular biology techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Dispersion of Carbon Nanotubes.

The invention provides a method for the dispersion of bundled carbon nanotubes by contacting the nanotubes with a stabilized solution of nucleic acid molecules.

Carbon Nanotubes

Carbon nanotubes of the invention are generally about 0.5-2 nm in diameter where the ratio of the length dimension to the narrow dimension, i.e., the aspect ratio, is at least 5. In general, the aspect ratio is between 10 and 2000. Carbon nanotubes are comprised primarily of carbon atoms, however may be doped with other elements, e.g., metals. The carbon-based nanotubes of the invention can be either multi-walled nanotubes (MWNTs) or single-walled nanotubes (SWNTs). A MWNT, for example, includes several concentric nanotubes each having a different diameter. Thus, the smallest diameter tube is encapsulated by a larger diameter tube, which in turn, is encapsulated by another larger diameter nanotube. A SWNT, on the other hand, includes only one nanotube.

Carbon nanotubes (CNT) may be produced by a variety of methods, and are additionally commercially available. Methods of CNT synthesis include laser vaporization of graphite (A. Thess et al. *Science* 273, 483 (1996)), arc discharge (C. Journet et al., *Nature* 388, 756 (1997)) and HiPCo (high pressure carbon monoxide) process (P. Nikolaev et al. *Chem. Phys. Lett.* 313, 91-97 (1999)). Chemical vapor deposition (CVD) can also be used in producing carbon nanotubes (J. Kong et al. *Chem. Phys. Lett.* 292, 567-574 (1998); J. Kong et al. *Nature* 395, 878-879 (1998); A. Cassell et al. *J. Phys. Chem.* 103, 6484-6492 (1999); H. Dai et al. *J. Phys. Chem.* 103,11246-11255 (1999)).

Additionally CNT's may be grown via catalytic processes both in solution and on solid substrates (Yan Li, et al., *Chem. Mater.;* 2001; 13(3); 1008-1014); (N. Franklin and H. Dai *Adv. Mater.* 12, 890 (2000); A. Cassell et al. *J. Am. Chem. Soc.* 121, 7975-7976 (1999)).

Nucleic Acid Molecules

Nucleic acid molecules of the invention may be of any type and from any suitable source and include but are not limited to DNA, RNA and peptide nucleic acids. The nucleic acid molecules may be either single stranded or double stranded and may optionally be functionalized at any point with a variety of reactive groups, ligands or agents. The nucleic acid molecules of the invention may be generated by synthetic means or may be isolated from nature by protocols well known in the art (Sambrook supra).

It should be noted that functionalization of the nucleic acids are not necessary for their association with CNT's for the purpose of dispersion. Functionailzation may be of interest after the CNT's have been dispersed and it is desired to bind other moieties to the nucleic acid or immobilize the carbon nanotube-nucleic acid complex to a surface through various functionalized elements of the nucleic acid. As used herein nucleic acids that are used for dispersion, typically lack functional groups and are referred to herein as "unfunctionalized."

Peptide nucleic acids (PNA) are particularly useful in the present invention as they possess the double functionality of both nucleic acids and peptides. Methods for the synthesis and use of PNA's are well known in the art, see for example Antsypovitch, S. I. *Peptide nucleic acids: structure Russian Chemical Reviews* (2002), 71(1), 71-83.

The nucleic acid molecules of the invention may have any composition of bases and may even consists of stretches of the same base (poly A or polyT for example) without impairing the ability of the nucleic acid molecule to disperse the bundled nanotube. Preferably the nucleic acid molecules will be less than about 2000 bases where less than 1000 bases is preferred and where from about 5 bases to about 1000 bases is most preferred. Generally the ability of nucleic acids to disperse carbon nanotubes appears to be independent of sequence or base composition, however there is some evidence to suggest that the less G-C and T-A base-pairing interactions in a sequence, the higher the dispersion efficiency, and that RNA and varieties thereof is particularly effective in dispersion and is thus preferred herein. Nucleic acid molecules suitable for use in the present invention include but are not limited to those having the general formula:

1. An wherein n=1-2000;
2. Tn wherein n=1-2000;
3. Cn wherein n=1-2000;
4. Gn wherein n=1-2000;
5. Rn wherein n=1-2000, and wherein R may be either A or G;
6. Yn wherein n=1-2000, and wherein Y may be either C or T;
7. Mn wherein n=1-2000, and wherein M may be either A or C;
8. Kn wherein n=1-2000, and wherein K may be either G or T;
9. Sn wherein n=1-2000, and wherein S may be either C or G;
10. Wn wherein n=1-2000, and wherein W may be either A or T;
11. Hn wherein n=1-2000, and wherein H may be either A or C or T;
12. Bn wherein n=1-2000, and wherein B may be either C or G or T;
13. Vn wherein n=1-2000, and wherein V may be either A or C or G;
14. Dn wherein n=1-2000, and wherein D may be either A or G or T; and
15. Nn wherein n=1-2000, and wherein N may be either A or C or T or G;

In addition the combinations listed above the person of skill in the art will recognize that any of these sequences may have one or more deoxyribonucleotides replaced by ribonucleotides (i.e., RNA or RNA/DNA hybrid) or one or more sugar-phosphate linkages replaced by peptide bonds (i.e. PNA or PNA/RNA/DNA hybrid).

Ligand Incorporation

It is contemplated that ligands may be introduced into the nucleic acid molecules in a variety positional orientations and numbers. For example ligands can be incorporated into one or both strands of a duplex nucleic acid analyte. Positionally, ligands can be incorporated either at the 5' or 3' ends of the analyte or incorporated on internal bases within the nucleic acid sequence, but incorporation internally is generally preferred.

The method of incorporation of the ligand into the nucleic acid sequences may be accomplished either by chemical or enzymatic means, or by direct incorporation of ligand labeled bases into the target sequence. In a preferred approach, ligand incorporated sequences are prepared using ligand labeled bases or primers during polymerase chain reaction. Ligand incorporation can be accomplished either through the incorporation of primers modified with ligand(s) or by using ligand labeled dNTPs. Ligand labeled primers can be prepared using standard oligonucleotide cyanoethyl phosphoramidite chemistry by substituting selected bases with ligand modified phosphoramidite bases during primer synthesis. Alternatively, if primers are prepared with modified bases containing a linkable molecular spacer, the ligands can be chemically linked to the spacer after primer synthesis. Another method would make use of ligand labeled dNTPs or amino modified dNTPs which can be incorporated into a target nucleic acid sequence during the amplification procedure.

There are several advantages to synthesis of ligand incorporated nucleic acid sequences by PCR. For example, where labeled primers are used, it is possible to control both the positioning and number of ligands within one or both strands of the target sequence by the appropriate placement of the ligand in the primers.

Of particular interest in the present invention is the incorporation of binding pairs into the nucleic acid molecule. Where a nucleic acid is associated with a carbon nanotube, the use of specific binding pairs enables the placement of the nucleic acid portion at a specific point of attachment and facilitates the rationale design of nano-devices and structures. Members of specific binding pairs suitable for use in practicing the invention can be of the immune or non-immune type. Immune specific binding pairs are exemplified by antigen/antibody systems or hapten/anti-hapten systems. The antibody member, whether polyclonal, monoclonal or an immunoreactive fragment thereof, of the binding pair can be produced by customary methods familiar to those skilled in the art. The terms "immunoreactive antibody fragment" or "immunoreactive fragment" refer to fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-steptavidin, folic acid-folate binding protein, complementary probe nucleic acids, Proteins A, G, and immunoglobulins, etc. Also included are non-immune binding pairs which form a covalent bond with each other: exemplary covalent binding pairs include sulfhydryl reactive groups such as maleimides and haloacetyl derivatives and amine reactive groups such as isothiocyanates, succinimidyl esters and sulfonyl halides, etc. M. N. Bobrow, et al., *J. Immunol. Methods,* 125, 279, (1989).

Binding pairs particularly suitable or use in the present invention include but are not limited to immune-type binding pairs, such as antigen/antibody or hapten/anti-hapten systems as well as glutathione-S-transferase/glutathione, 6× histidine Tag/Ni-NTA, streptavidin/biotin, S-protein/S-peptide, cutinase/phosphonate inhibitor, antigen/antibody, hapten/anti-hapten, folic acid/folate binding protein, and protein A or G/immunoglobulins. Binding pairs may also include charged moieties as for example, a negatively charged phosphate backbone of a nucleic acid molecule, with the second member being a positively charged surface.

Nucleic Acid Stabilization

Once the nucleic acid molecule has been prepared it may be stabilized in a suitable solution. It is preferred if the nucleic acid molecules are in a relaxed secondary conformation and only loosely associated with each other to allow for the greatest contact by individual strands with the carbon nanotubes. Stabilized solutions of nucleic acids are common and well known in the art (see Sambrook supra) and typically include salts and buffers such as sodium and potassium salts, and TRIS (Tris(2-aminoethyl)amine), HEPES (N-(2-hydroxyethyl)piperazine-N'-(2-ethanesulfonic acid), and MES(2-(N-Morpholino)ethanesulfonic acid. Preferred solvents for stabilized nucleic acid solutions are those that are water miscible where water is most preferred.

Once the nucleic acid molecules are stabilized in a suitable solution they may be contacted with a population of bundled carbon nanotubes. It is preferred, although not necessary if the contacting is done in the presence of an agitation means of some sort. Typically the agitation means employs sonication for example, however may also include, devices that produce high shear mixing of the nucleic acids and nanotubes (i.e. homogenization), or any combination thereof. Upon agitation the carbon nanotubes will become dispersed and will form nanotube-nucleic acid complexes comprising at least one nucleic acid molecule loosely associated with the carbon nanotube by hydrogen bonding or some non-covalent means.

The process of agitation and dispersion may be improved with the optional addition of nucleic acid denaturing substances to the solution. Common denaturants include but are not limited to formamide, urea and guanidine. A non-limiting list of suitable denaturants may be found in Sambrook supra.

Additionally temperature during the contacting process will have an effect on the efficacy of the dispersion. Agitation at room temperature or higher was seen to give longer dispersion times whereas agitation at temperatures below room temperature (23° C.) were seen to give more rapid dispersion times where temperatures of about 4° C. are preferred.

Recovery of Dispersed Nanotubes

Once the nanotube-nucleic acid molecule complexes are formed they must be separated from solution. Where the nucleic acid has been functionalized by the addition of a binding pair for example separation could be accomplished by means of immobilization thought the binding pair as discussed below. However, where the nucleic acid has not been functionalized an alternate means for separation must be found. Applicants have provided a novel separation method involving either gel electrophoresis chromatography or a phase separation method that is rapid and facile and permits the separation of nanotube-nucleic acid complexes into discreet fractions based on size or charge. These methods have been applied to the separation and recovery of coated nanoparticles (as described in U.S. Ser. No. 10/622,889 incorporated herein by reference) and have been found useful here.

Gel electrophoresis is a commonly used method in biochemistry and molecular biology to separate macromolecules such as proteins and nucleic acids. The gel serves as a sieving medium to separate the macromolecules on the basis of size. In the present invention, the gel can be made from agarose or polyacrylamide. Methods for preparing suitable gels are well known and exemplified in Sambrook, supra, particularly Chapter 6 (entirely incorporated herein by reference). Suitable agarose gels have an agarose concentration between 0.6 and 6% (weight per volume), while suitable polyacrylamide gels have an acrylamide concentration between 3.5 and 20% (weight per volume). It is well known in the art that the concentration of the gel to be used depends on the size of the molecules being separated. Specifically, higher gel concentrations provide better separation for smaller molecules, while lower gel concentrations are used to separate larger molecules. The gel concentration to be used for a given nanoparticle fractionation can be determined by routine experimentation. The preferred gel of the present invention is a 1% or lower agarose gel.

In order to determine the average particle size of the complexes a densifying agent may be added to an aqueous solution of the complexes. The purpose of densifying agent is to increase the specific gravity of the nanoparticle solution to facilitate loading of the solution into the gel. Suitable densifying agents are well known and include, but are not limited to, glycerol, sucrose, and Ficoll (a nonionic, synthetic polymer of sucrose, approximate molecular weight of 400,000, available from Sigma, St. Louis, Mo.). The complex solution is then added to the wells in the gel. The complexes migrate according to their apparent molecular weight and size of any particular complex may be determined by using molecular weight standards.

Alternatively the complexes may be separated by two phase separation methods. In this method nanotube-nucleic acid complexes in solution are fractionated by adding a substantially water-miscible organic solvent in the presence of an electrolyte. The amount of the substantially water-miscible organic solvent added depends on the average particle size desired. The appropriate amount can be determined by routine experimentation. Typically, the substantially water-miscible organic solvent is added to give a concentration of about 5% to 10% by volume to precipitate out the largest particles. The complexes are collected by centrifugation or filtration. Centrifugation is typically done using a centrifuge, such as a Sorvall® RT7 PLUS centrifuge available from Kendro Laboratory Products (Newtown, Conn.), for about 1 min at about 4,000 rpm. For filtration, a porous membrane with a pore size small enough to collect the complex size of interest can be used. Optionally, sequential additions of the substantially water-miscible organic solvent are made to the complex solution to increase the solvent content of the solution and therefore, precipitate out complexes of smaller sizes.

Immobilization/Association of Nanotube-Nucleic Acid Complexes

Once formed the dispersed nanotube-nucleic acid complexes containing ligands or binding pairs may be either immobilized on a solid substrate or rationally associated with other complexes in a process of nano-device fabrication.

For example, where the nucleic acid molecule has been functionalized with a first member of a binding pair, it may be immobilized on a solid support containing a second member of the binding pair. Solid supports suitable for such purposes are common and well known in the art and include but are not limited to, silicon wafers, synthetic polymer supports, such as polystyrene, polypropylene, polyglycidylmethacrylate, substituted polystyrene (e.g., aminated or carboxylated polystyrene; polyacrylamides; polyamides; polyvinylchlorides, etc.), glass, agarose, nitrocellulose, nylon, nickel grids or disks, silicon wafers, carbon supports, aminosilane-treated silica, polylysine coated glass, mica, and semiconductors such as Si, Ge, and GaAs. Method for incorporating binding pair members onto the surface of solid supports is also and advanced art (see for example, *Immobilized Enzymes*, Inchiro Chibata, Halsted Press, New York (1978) and Cuatrecasas, *J. Bio. Chem.*, 245: 3059 (1970)).

Preferred binding pairs for immobilization of the present complexes are biotin/streptavidin or biotin/avidin.

Alternatively it will be possible to immobilize the complexes of the invention by direct interaction between nucleic acid molecules. For example, nucleic acid molecules in the dispersion sample may be chosen or designed to incorporate a specific hybridization domain that will hybridize with a specific complementary sequence. Nucleic acids having the complement sequence to the hybridization domain may be placed on the surface of the support and the complex captured by hybridization. Immobilization of nucleic acids to a solid support is common and well known in the art and may be accomplished for example using ultraviolet irradiation, baking, capillary transfer or vacuum transfer. Examples of nucleic acid immobilization on nitrocellulose and other suitable supports are given in Kalachikov, S. M., et al., *Bioorg. Khim.*, 18, 52, (1992) and Nierzwicki-Bauer, et al., *Biotechiques*, 9, 472, (1990).

It will be appreciated by the person of skill in the art that the above mentioned interactions that enable the immobilization of the complexes of the invention may be equally employed to associate individual complexes with other complexes in a specific fashion. For example, a biotin containing complex may associate with a streptavidin containing complex or the hybridization domain of one nucleic acid molecule may be designed to bind to a similar domain on another complex.

In this fashion complexes may be rationally associated or immobilized to facilitate device fabrication.

Metallization of Associated or Immobilized Complexes

Where it is desired to use the complexes of the invention, either immobilized or associated in a particular conformation, as electrical conductors, the complexes can be metallized according to methods well known in the art. So for example it is well known in the art to sputter or evaporatively coat nanoscale structures with metals such as gold or platinum, respectively, in order to stabilize and image the structures (Schnur, J. M. et al. (1987) *Thin Solid Films* 152, 181-206; Markowitz, M. et al. (1992) *Thin Solid Films* 224, 242-7), rhapidosomes (Pazirandeh, M. et al. (1992) *Biomimetics* 1, 41), DNA (Braun, E. et al. (1998) *Nature* 391, 775-8) and microtubules (Kirsch, R. et al. (1997) *Thin Solid Films* 305, 248-253).

Metallized nanotube-nucleic acid complexes of the invention will be useful as nanowires or molecular interconnects in the fabrication of nano-devices. It will be expected for example that these metallized structures could be arrayed in a crossed arrangement, where the distance between adjacent complex can be controlled by the potential difference between them, then the array could be used as a non-volatile memory device similar to that proposed by Leiber and collaborators (Rueckes T. et al. (2000). *Science* 289, 94-97) for carbon nanotubes. Semiconducting complexes could find use in 3-terminal gated devices which can be used directly as switches, amplifiers or logic gates. By linking the metalized complexes with organic semiconductors, it may be possible to develop 2-terminal switching devices, showing, for example, negative differential resistance (e.g. Fan et al. (2002) *JACS* 124, 5550-5560). Other possible applications include point sources for emission in field-emission display devices and as conductive inclusions in conductive coatings.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular biology techniques used in the Examples are well known in the art and are described by Sambrook, J., Fritsch, E. F. and Maniatis, *T. Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "h" means hour(s), "min" means minute(s), "sec" means second(s), "d" means day(s), "mL" means milliliters, "L" means liters.

General Procedure for Dispersion of Carbon Nanotubes by Nucleic Acid

The single wall carbon nanotubes were made by the HiPCO process, either purified or unpurified, and were purchased from CNI (Houston, Tex.). The materials were used as received without further modification. Single-stranded DNA (ssDNA) oligonucleotides were purchased from Integrated DNA Technologies, INC (Coralville, Iowa). Yeast tRNA was purchased from Sigma (St. Louis, Mo.). RNA homopolymers poly(A), poly(C) and poly(U) were purchased from Amersham Biosciences (Piscataway, N.J.). In a typical experiment, 10 mg of CNT were suspended in 10 mL of 1×SSC buffer (0.15M NaCl, 0.015M sodium citrate), then sonicated for 2 min with a TORBEO 130-Watt Ultrasonic Processor (Cole-Parmer Instrument Company, Vernon Hills, Ill.). Nucleic acids were dissolved in $H_2O$ to give a final concentration of 10 mg/mL. 50 µL of the CNT suspension and 5 µL of 10 mg/mL nucleic acid solution were added to 200 µL of $H_2O$ to give a final volume of 255 µL. The mixture was sonicated for 3 min., followed by 90 min of centrifugation at 16,000 g (Biofuge fresco, Kendro Laoratory Products, Newtown, Conn.). The supernatant was then removed for spectroscopic measurement. Absorption spectra from 400 nm to 900 nm were recorded using Ultrospec 3300 UV-Vis spectrophotometer (Amersham Biosciences, Piscataway, N.J.). The 730 nm peak was taken as a measure of the yield of the dispersion process.

Example 1

Dispersion of Carbon Nanotubes by Single-stranded DNA: Sequence Dependence

In this experiment, purified single wall carbon nanotubes (HiPCO) were used. Following the procedure described above, the dispersion efficiency of a variety of sequences was examined. The sequences used include:

(N)90: where N stands for a random mix of G, A, T and C, the total length is 90 bases;
(C/A)90: where C/A stands for a random mix of C and A, the total length is 90 bases;
(G/A)90: where G/A stands for a random mix of G and A, the total length is 90 bases;
(G/T)90: where G/T stands for a random mix of G and T, the total length is 90 bases;
(C/T)90, 60, 30: where C/T stands for a random mix of C and T, the total length is 90, 60 and 30 bases, respectively;
C60: a homopolymer of C with 60 bases long;
T60: a homopolymer of T with 60 bases long.

Results from above sequences are shown in FIG. 1. In general, the less G-C and T-A base-pairing interactions in a sequence, the higher the dispersion efficiency.

Example 2

Dispersion of Carbon Nanotubes by Single-stranded DNA: Effect of Sonication

Figure 2:
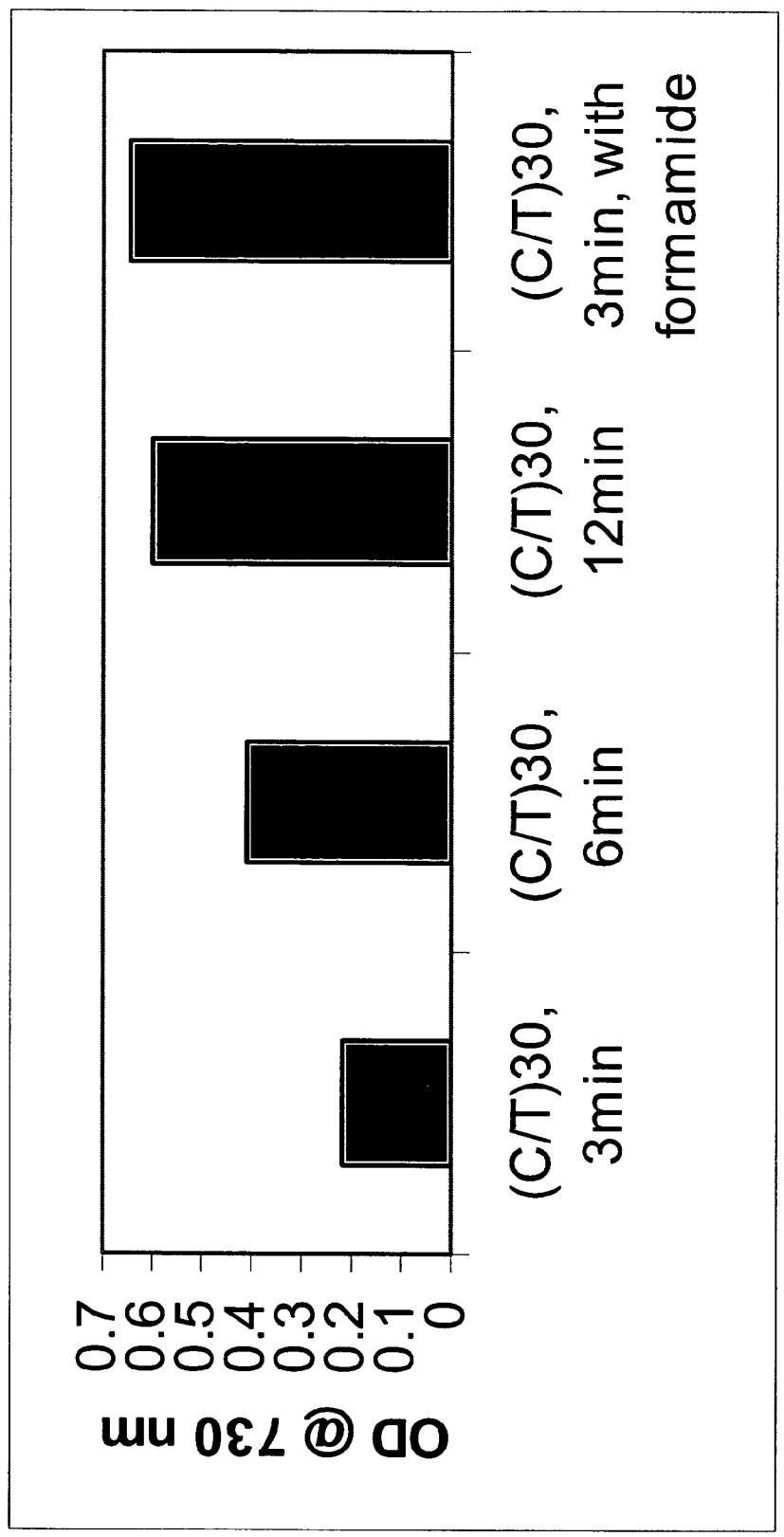
FIG. 2 is a graph of optical density measurements illustrating the dispersion efficiency of a particular sequence as a function of duration of sonication and with addition of formamide.

In this experiment, purified single wall carbon nanotubes (HiPCO) were used. Following the procedure described above, the dispersion efficiency of a particular sequence (C/T)30 as a function of duration of sonication examined. As shown in FIG. 2, the longer the sonication, the more the dispersed CNT. This was found to be true for other sequences tested when sonication time is shorter than 15 minute. Beyond 15 min. duration, there is no further improvement in dispersion efficiency.

Example 3

Dispersion Carbon Nanotubes by Single-stranded DNA: Effect of Denaturants

In this experiment, purified single wall carbon nanotubes (HiPCO) were used. Following the procedure described above, the dispersion efficiency of a particular sequence (C/T)30 in the absence and presence of nucleic acid denaturant formamide. As shown in FIG. 2, denaturant improves the final yield by a factor of 3 for this particular sequence. Other experiments showed that denaturants (such as formamide and urea) in general improve dispersion efficiency by 2 to 3 fold.

Example 4

Dispersion of Carbon Nanotubes by Single-stranded DNA vs. SDS

Figure 3:
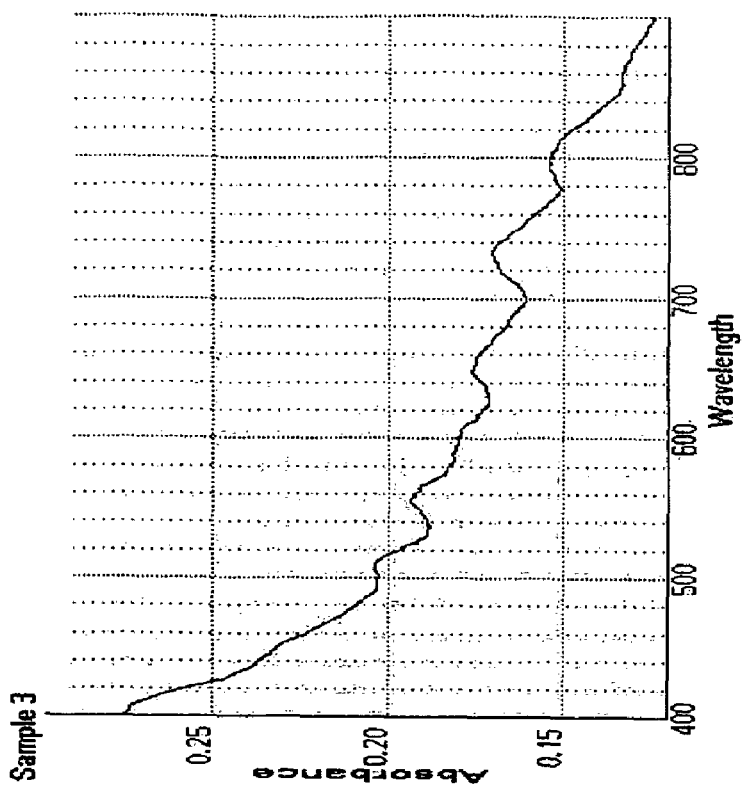
FIG. 3 is a graph of optical density measurements comparing the dispersion efficiency of carbon nanotubes by ssDNA (FIG. 3A) versus surfactant (FIG. 3B).
Figure 3:
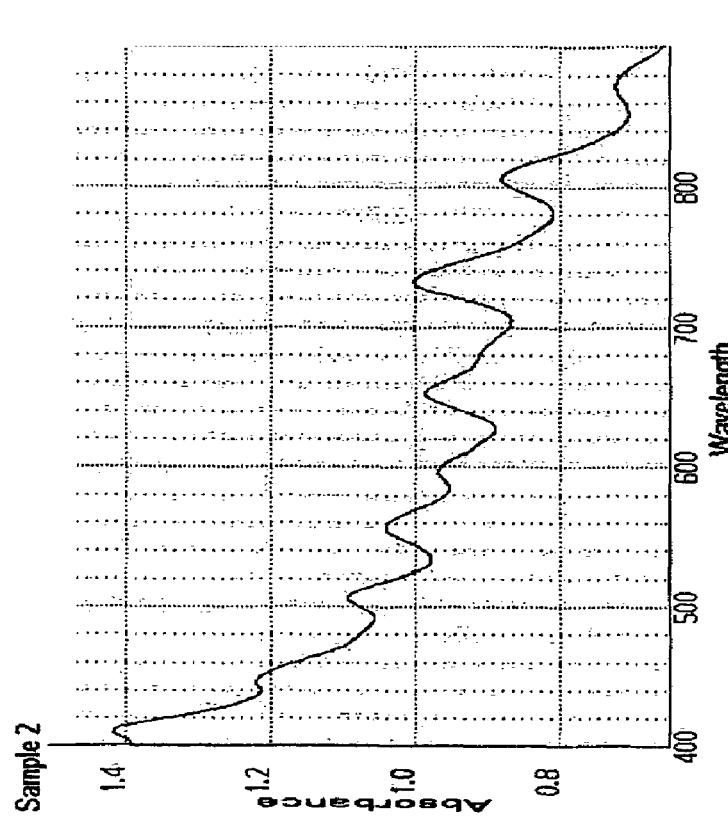

In this experiment, purified single wall carbon nanotubes (HiPCO) were used. Two dispersion tests were set up in this Example, following general procedures described above. In the first one, (C/T)30 DNA was used. In the second sample, no DNA was used and 175 µl of $H_2O$ plus 25 µl of 10% SDS (sodium dodecyl sulfate, purchased from Sigma, St. Louis, Mo.) aqueous solution were added in place of 200 μl of H$_2$O. As shown in FIG. 3, the yield from DNA-dispersed CNT was at least five times higher that from SDS-dispersed CNT. Moreover, the degree of dispersion by DNA is higher that by SDS, as judged by the line-width of absorption peaks.

Example 5

Dispersion of Carbon Nanotubes by RNA

Figure 4:
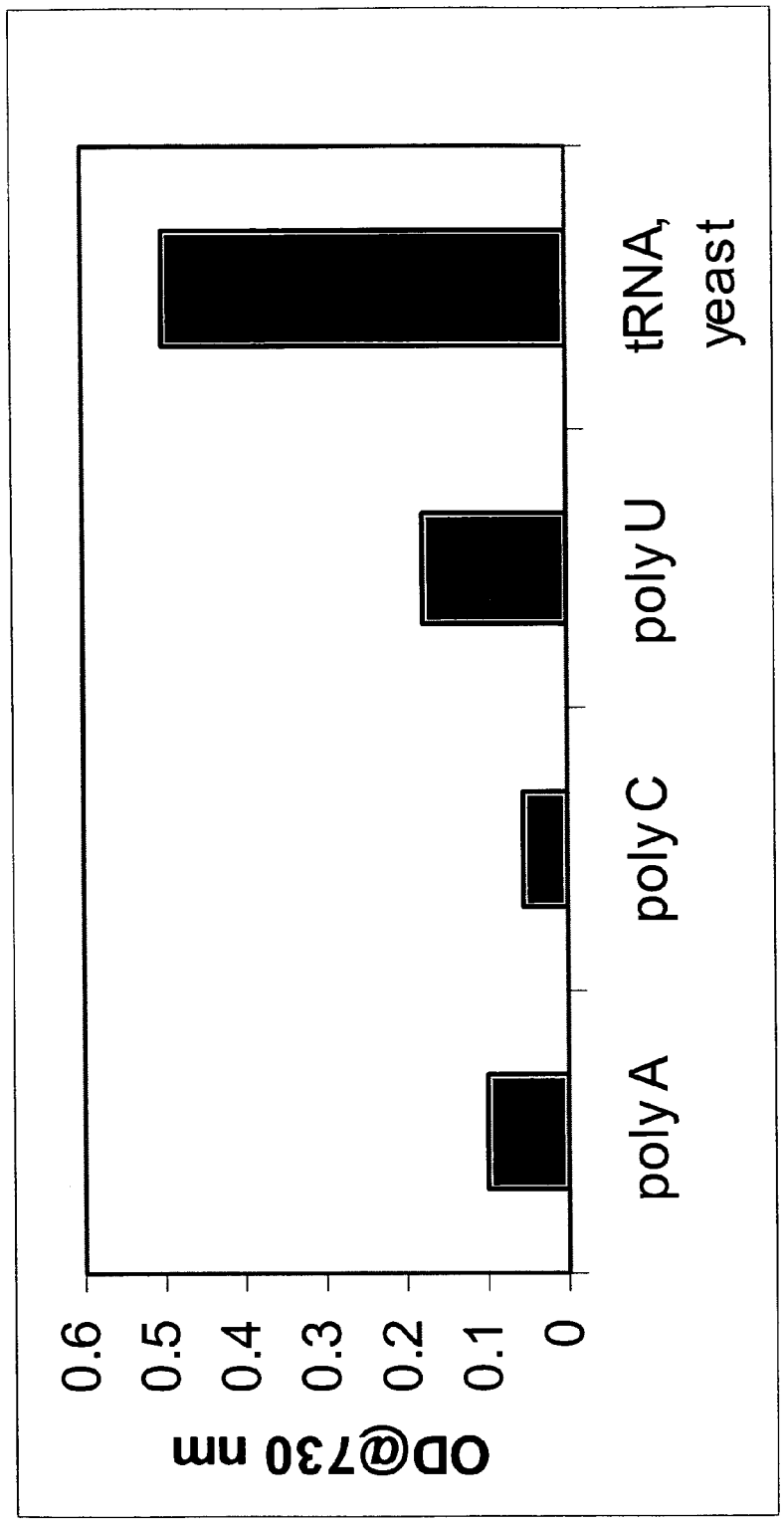
FIG. 4 is a graph of optical density measurements to illustrate the carbon nanotube dispersion efficiency by RNA.

In this experiment, unpurified single wall carbon nanotubes (HiPCO) were used. Dispersion experiments were performed as described above, except that RNA (poly A, poly C, poly U and yeast tRNA) were used. The results shown in FIG. 4 indicate that RNA can also disperse CNT.

Example 6

Dispersion Carbon Nanotubes by Single-stranded DNA: Effect of Sonication Temperature In this experiment, unpurified single wall carbon nanotubes (HiPCO) were used. Following procedure described above, we have examined dispersion efficiency of a particular sequence (C/T)30 as a function of sonication temperature. In the first test, sonication was done as described in above. In the second test, sample was prepared the same way as the first test, except that sample was held in an ice-water bath during sonication. The yield of carbon nanotube dispersion from the second test was determined to be four times higher than the first test. This temperature effect was found to be true for other sequences as well.

Example 7

Precipitation of DNA and RNA Dispersed Carbon Nanotubes

In this experiment, both purified and unpurified single wall carbon nanotubes (HiPCO) were tested. Dispersion experiments were performed as described above. In a typical experiment, 200 μl of either DNA or RNA dispersed carbon nanotube solution at concentration of ~0.1 mg/ml were mixed with equal volume of ethanol. Immediately after mixing, aggregation of carbon nanotube in solution was visible. After 1 min centrifugation at 16,000 g (Biofuge fresco, Kendro Laoratory Products, Newtown, Conn.), the supernatant solution became clear and all the carbon nanotubes went to the pellet. It was found that the pellet could be re-suspended into aqueous solution again.

Example 8

Figure 5:
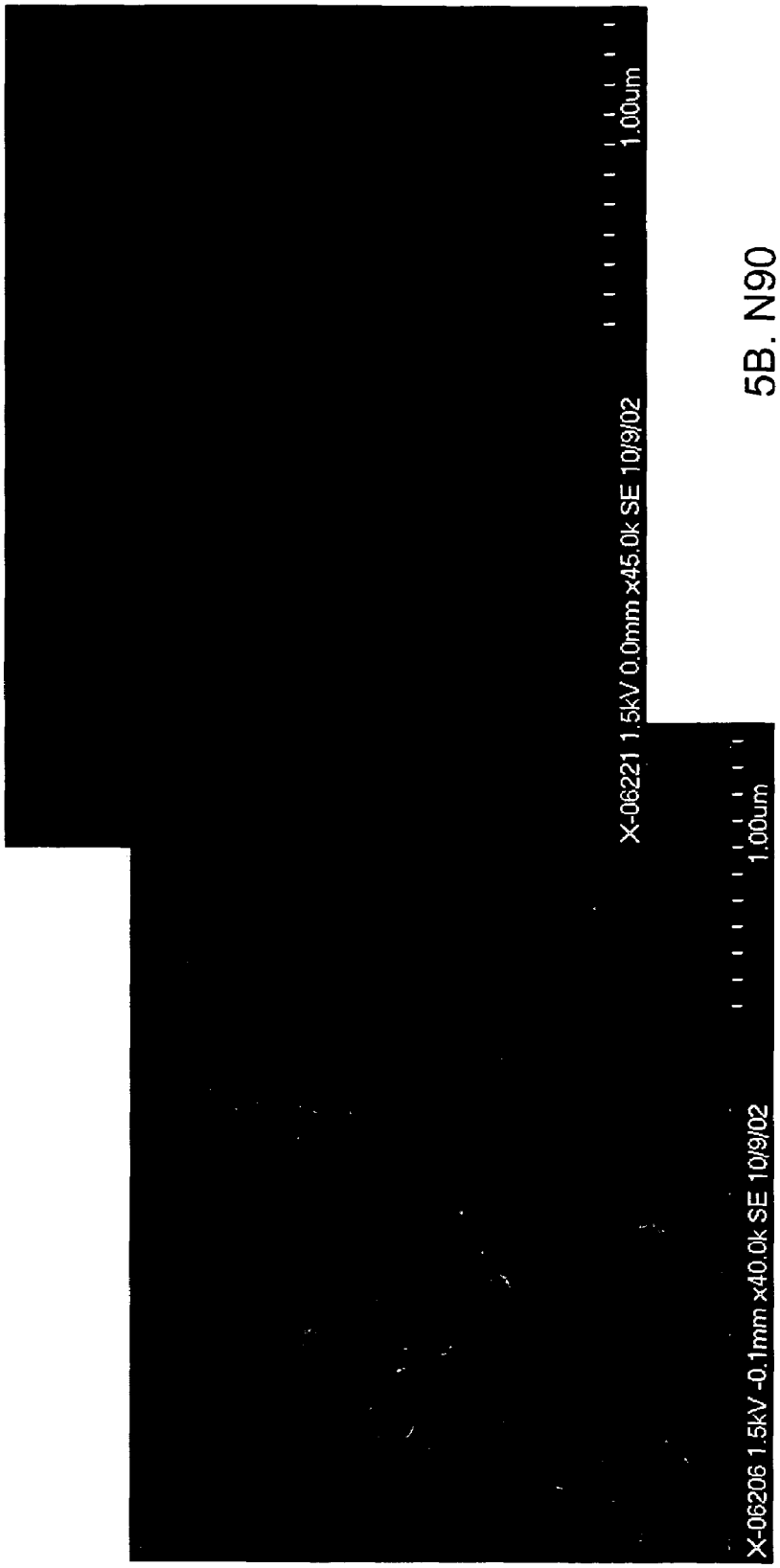
FIG. 5 is an electronmicrograph illustrating immobilization of DNA dispersed carbon nanotubes through biotin-streptavidin interaction.

Immobilization of DNA Dispersed Carbon Nanotubes Through Biotin-Streptavidin Interaction In this experiment, unpurified single wall carbon nanotubes (HiPCO) were used. Dispersion experiments were performed as described in above. Two ssDNAs were tested: 1) random 90-mer (N90 hereafter); 2) random 90-mer with biotinylated 5' end (biotin-N90 hereafter). Streptavidin-coated agarose beads were purchased from Sigma (St. Louis, Mo.), and were used as received. Two samples were prepared. Sample 1: 100 μl of the agarose beads were mixed with 100 μl of N90 dispersed carbon nanotube (~0.1 mg/ml). After 30 min of incubation, the beads were spun down and washed with 0.5 mL of 1×SSC solution for 3 times. Sample 2: same as Sample 1, except biotin-N90 dispersed carbon nanotubes were used. After washing, one could notice that the pellet from Sample 2 was darker than Sample 1, indicating carbon nanotube binding to the beads. The two samples were analyzed by SEM (Scanning Electron Microscopy). The results shown in FIG. 5A and 5B confirmed that biotin-N90 but not N90 dispersed carbon nanotubes were trapped on the surface of the beads.

Example 9

Atomic Force Microscopy

Figure 6:
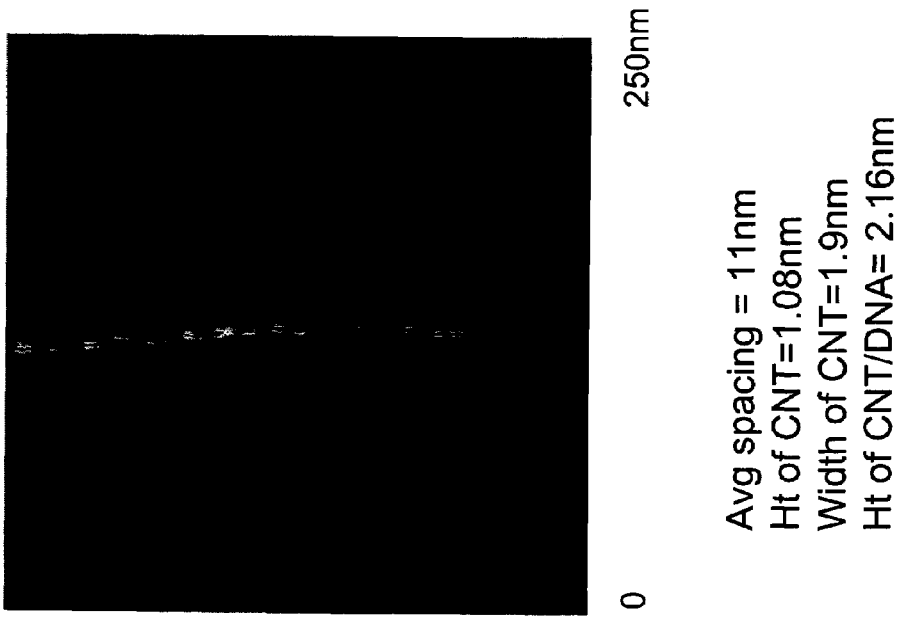
FIG. 6 is an electronmicrograph taken via atomic force microscopy of an isolated carbon nanotube wrapped with DNA.
Figure 7:
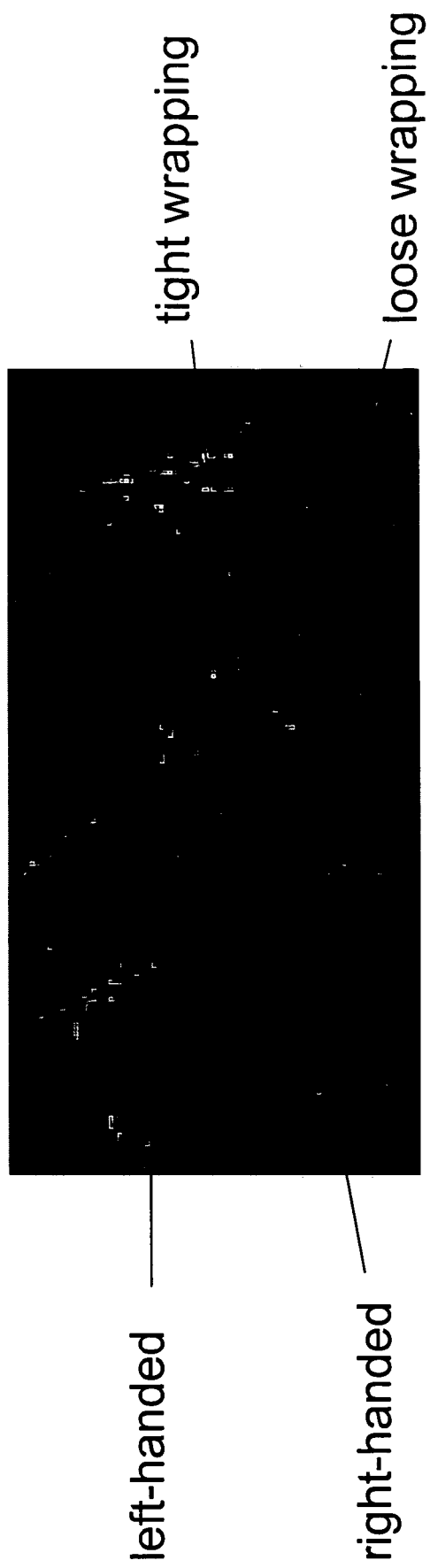
FIG. 7 is an electronmicrograph taken via atomic force microscopy showing different modes of DNA wrapping on carbon nanotubes.

The sample solution from Example 2 was deposited onto a piece of mica pre-treated with 1 M MgSO4 solution to enhance DNA adsorption, and rinsed with water and dried prior to measurement. Tapping mode was used to acquire the images under ambient conditions (Digital Instruments Dimension 3100, Woodbury, N.Y.). FIG. 6 shows an isolated tube with 1 nm diameter, wrapped by DNA with an average spacing of 11 nm. The width of the tube is 1.9 nm and the height is of the CNT/DNA=2.16 nm. FIG. 7 shows different modes of DNA wrapping on different CNTs.

What is claimed is:
1. A method for the production of a dispersed, carbon Nanotube—nucleic acid complex comprising:
   a) providing a stabilized solution of single stranded nucleic acid molecules;
   b) contacting a population of unfunctionalized, single walled carbon nanotubes with an effective amount of the stabilized nucleic acid solution of step (a) for a time sufficient for the single stranded nucleic acid molecules to associate with the carbon nanotubes by non-covalent means to form a dispersed, carbon nanotube—nucleic acid complex; and
   c) optionally recovering the dispersed, carbon nanotube—nucleic acid complex.

2. A method according to claim 1 wherein the nucleic acid solution is aqueous.

3. A method according to claim 1 wherein the contacting is done in the presence of an agitation means.

4. A method according to claim 3 wherein the agitation means is selected from the group consisting of sonication, high shear mixing, or any combination thereof.

5. A method according to claim 1 wherein the contacting is done in the presence of a denaturing agent.

6. A method according to claim 1 wherein the contacting is done at about 4° C.

7. A method according to claim 1 wherein the nucleic acid molecules are selected from the group consisting of: single stranded DNA, single stranded RNA and single stranded PNA.

8. A method according to claim 7 wherein the single stranded nucleic acid molecules are synthetic.

9. A method according to claim 7 wherein the single stranded nucleic acid molecule is selected from the group consisting of:
   1. An wherein n=1-2000;
   2. Tn wherein n=1-2000;
   3. Cn wherein n=1-2000;
   4. Gn wherein n=1-2000;
   5. Rn wherein n=1-2000, and wherein R may be either A or G;
   6. Yn wherein n=1-2000, and wherein Y may be either C or T;

7. Mn wherein n=1-2000, and wherein M may be either A or C;
8. Kn wherein n=1-2000, and wherein K may be either G or T;
9. Sn wherein n=1-2000, and wherein S may be either C or G;
10. Wn wherein n=1-2000, and wherein W may be either A or T;
11. Hn wherein n=1-2000, and wherein H may be either A or C or T;
12. Bn wherein n=1-2000, and wherein B may be either C or G or T;
13. Vn wherein n=1-2000, and wherein V may be either A or C or G;
14. Dn wherein n=1-2000, and wherein 0 may be either A or G or T; and
15. Nn wherein n=1-2000, and wherein N may be either A or C or T or G.

10. A method according to claim 1 wherein the single stranded nucleic acid molecules are from about 10 bases to about 1000 bases in length.

* * * * *